United States Patent [19]
Koster

[11] 3,994,156
[45] Nov. 30, 1976

[54] TESTING APPARATUS FOR CROP-MOISTURE CONTENT

[75] Inventor: Edward C. Koster, North Randall, Ohio

[73] Assignee: Koster Crop Tester Inc., North Randall, Ohio

[22] Filed: Oct. 28, 1975

[21] Appl. No.: 626,302

[52] U.S. Cl. .................................................. 73/76
[51] Int. Cl.² ............................. G01N 25/56;
[58] Field of Search ............ 73/76; 34/233; 338/316 219 374;375

[56] References Cited
UNITED STATES PATENTS

| | | | |
|---|---|---|---|
| 1,704,479 | 3/1929 | Kercher et al. | 219/364 |
| 2,732,632 | 1/1956 | Koster | 73/76 |
| 2,912,661 | 11/1959 | Balestrini | 338/316 |
| 3,670,143 | 6/1972 | Zenz | 338/316 |

Primary Examiner—James J. Gill
Assistant Examiner—Anthony V. Ciarlante
Attorney, Agent, or Firm—Cain and Henn

[57] ABSTRACT

A simple, rugged and inexpensive apparatus is provided by which the moisture content of any grain crop, various types of forage crops such as hay and straw, and the like, may be determined. The apparatus is portable, requires very little maintenance, and is as accurate as it is reliable. A crop sample of harvested material is placed in a confined zone through which warm air at a predetermined temperature is blown for a preselected period of time. The weight loss in moisture is observed and directly correlated to the remaining moisture content in the material.

3 Claims, 3 Drawing Figures

TESTING APPARATUS FOR CROP-MOISTURE CONTENT

BACKGROUND OF THE INVENTION

There are numerous methods utilizing technically sophisticated testing apparatus in which the moisture content of grain, hay, nuts, dried fruits, beans, and the like, may be measured. The accuracy of measurement is in part related to the complexity of the apparatus utilized and also to the skill of the persons conducting the test. It is impractical for a lone farmer or layman to purchase complicated testing apparatus for his private use, and traditionally, accurate measurements of moisture content are usually made by the operators of silos and granaries in which the crop is to be stored. These operators have a large financial stake in the accurate determination of moisture content of material to be stored. The ease with which stored material can be destroyed by spoilage, if the moisture content is out of a relatively narrow preferred range, is well known.

Since the moisture content of a harvest is of just as much interest to the farmer as to the large purchaser of the harvest, less expensive testing apparatus have been widely used, which permit a sufficiently accurate determination of moisture content to indicate to the farmer the optimum time of harvest for a particular crop. Such a device is disclosed in my U.S. Pat. No. 2,732,632 issued Jan. 31, 1956. Over the years, this testing apparatus has demonstrated its effectiveness and reliability time and time again.

The generally high prices of crops now prevalent, places a heavy responsibility on the farmer that a crop be harvested at such time as the moisture content is optimum. Further, it is essential that a determination of moisture content be both more accurate and reliably reproducible. The apparatus of this invention is an improvement on my prior apparatus and provides more accurate moisture content determination, and at the same time, a structurally more desirable apparatus.

SUMMARY OF THE INVENTION

It is a general object of this invention to provide a new and improved moisture testing apparatus for the determination of the moisture content of grain, beans, nuts, hay, straw, and other forage crops which are desirably harvested when the moisture content of the crop is within a relatively narrow range.

It is another general object of the invention to provide a new and improved testing apparatus which may be used by a relatively unskilled person to make an accurate determination of moisture content.

It is also a general object of the instant invention to provide a new and improved moisture testing apparatus fabricated from simple, easily assembled and disassembled components.

It is a specific object of this invention to provide a confined zone in which a substantial sample may be placed, through which confined zone heated air may be flowed unidirectionally without being recirculated, the air being heated by contact with a ribbon heating element above which a ceramic-encased thermostat is disposed.

It is another specific object of this invention to eliminate the inner liner of the aforementioned prior art device thereby making the components more accessible.

It is also a specific object of this invention to shield the thermostat from direct radiation of the heating element so as to increase its reliability and its life.

It is a further specific object of this invention to removably affix the top screen in the body of the heating assembly in a manner so as to permit replacement of the thermostat without disassembling the entire unit.

Still further objects of this invention include the provision of a new and improved ribbon heating element which uniformly heats the air flowing through a sample of material to be tested; of a simplified structure for ease of assembly and to minimize maintenance; the provision of a thermostat which has enhanced accuracy and long life; and the provision of a testing apparatus which may be fabricated and maintained with economy without sacrificing performance.

It is a still further object of this invention to provide a new and improved moisture testing apparatus obtaining one or more of the objects and advantages set forth above.

These and other objects, features and advantages of this invention will become apparent to those skilled in the art from the following description of preferred forms thereof, reference being had to the accompanying drawings and appended claims.

BRIEF DESCRIPTION OF THE DRAWINGS

In the drawings, which represent a preferred embodiment of the invention.

In the figures of the drawing, like reference numerals are used to denote like parts. Some of the parts have been dimensionally exaggerated for clarity of illustration and to facilitate the description of the operation of the apparatus.

DETAILED DESCRIPTION OF THE PREFERRED EMBODIMENTS

Figure 1:
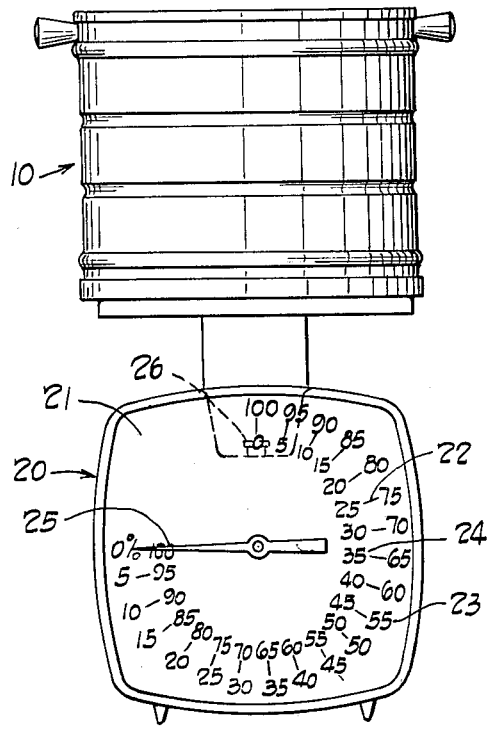
FIG. 1 is an elevational view of a special scale and crop sample container as is conventionally used.
Figure 3:
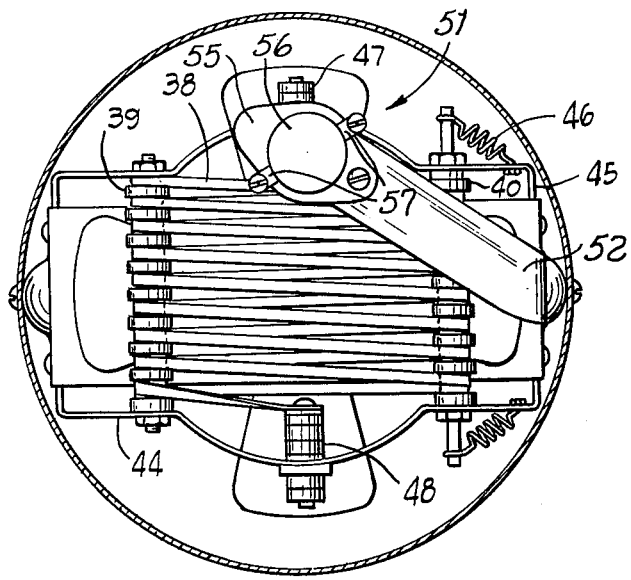
FIG. 3 is a horizontal section taken along the line 3—3 of FIG. 2 showing components of the new and improved heater unit.

The moisture tester includes three separable components which are used in combination to measure the moisture content of a crop sample. Referring to FIG. 1 there is shown a first component which is a sample container indicated generally by reference numeral 10, placed on a second component which is a special scale indicated generally by reference numeral 20. Referring to FIG. 3 there is shown a third component which is an electrically energized heater indicated generally by reference numeral 30. For use, the sample container 10 is nested on top of the heater so that air heated in the heater is flowed upwardly through the material. As will be readily apparent, the shape of each component is important only in so far as the lower portion of the sample container and the top portion of the heater can be snugly coupled so as to prevent substantial leakage of hot air; and the scale is adapted to support the sample container. Cylindrical components are conveniently used because of ease of fabrication and assembly and may be assembled as described in my U.S. Pat. No. 2,732,632.

The special scale 20 is of the same type as that shown and described in my aforesaid U.S. patent, and has a special scale face 21 having graduations 22 identified with numerals 23 from zero to 100 to indicate directly the percent moisture content of the sample. As will be seen, the moisture graduations are inscribed exteriorly of the circumscribed graduations, and decrease numerically clockwise on the special scale face. Interiorly of the circumscribed graduations there are inscribed numerals 24 from zero to 100 but in the reverse order of the numerals 23. The numerals 24 indicate directly the dry-matter content of the sample in the container 10. A pointer 25 moves counterclockwise as the weight on the scale decreases. A knob 26 is used to align pointer 25 with any graduation reference line 22. The scale may also carry a legend disclosing preferred ranges of moisture content of various harvested materials prior to storage or sale.

The forced air flow heater 30 provides drying air at an essentially steady temperature sufficiently high to evaporate the moisture in the sample without scorching the material. It will be recognized that the air temperature from the heater will vary somewhat depending upon the ambient temperature, but a preferred temperature is in the range from about 250° F to about 280° F. The heater consists of a cylindrical housing having an inlet 31 and an outlet 32, each provided with diffuser screens shown at 33 and 34 to direct a generally equal rate of air flow to each unit area under the sample to be dried. The diffuser screens 33 and 34 also serve to filter out foreign matter through the heater. Feet 35 support the heater unit and provide an inlet for the air. An electrical motor 36 drives the fan 37 to give a forced air flow over ribbon heating element 38.

Referring now to FIG. 3 showing a plan view of the heater components, there is shown the ribbon element 38 interlaced between a pair of parallel horizontally spaced apart ceramic supports 39 and 40. Ceramic support 39 is fixedly mounted in a support bracket 44 and ceramic support 40 is movably mounted in support bracket 45. Spring means 46 between the support bracket 45 and the ceramic support 40 provide a biasing force which maintains tensions on the ribbon element 38. As the ribbon heating element is heated and expands, the ceramic support 40 is moved laterally in a direction away from the ceramic support 39 because of the force exerted by the springs 46. When the the ribbon element 38 cools down, the ribbon element contracts and the springs 46 are extended. The ribbon element is connected to terminals 47 and 48 so that the ribbon element and thermostat 51 may be connected to a power line separate from the motor 36, or if desired it may be connected in parallel with the motor 36.

A thermostat indicated generally at 51 is mounted at one end of an elongated thermostat bracket 52 the other end of which is affixed to the heater body in such a way that the thermostat 51 is cantilevered above the ribbon heating element 38 disposed thereabove, to provide the optimum control of the heat. The thermostat 51 is enclosed provided with a ceramic body 55 and a metal shield 56 is positioned over a sensing element 57 (partially shown). This combination protects the sensing element from direct radiation from the ribbon heating element, thus increasing its accuracy and its useful life.

Figure 2:
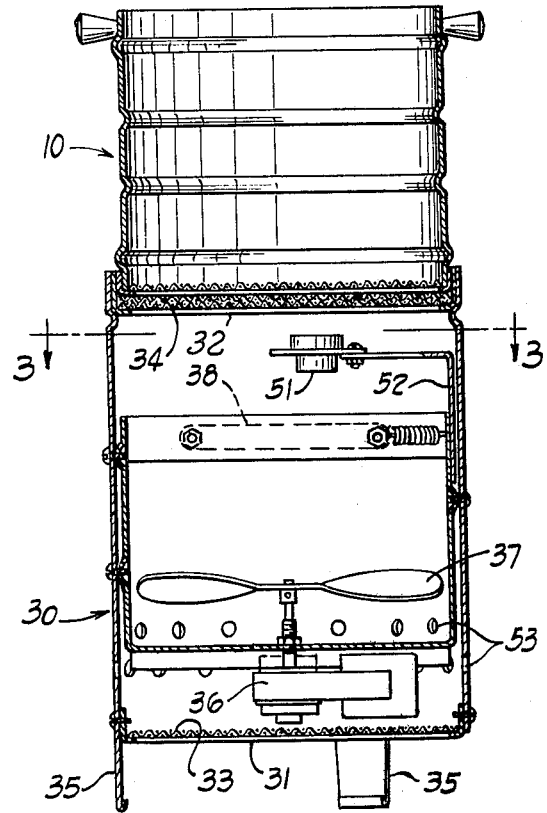
FIG. 2 is a vertical section of the crop sample container nested upon the new and improved heater unit of the moisture testing apparatus.

Reverting to FIG. 2, the top screen 34 is installed so that it can be removed from the top of the heater unit. This eliminates the necessity of disassembling the entire unit when the thermostat is replaced. The bottom screen 33 is installed in the lower portion of the heater body using screw fastening means which directly attach the screen to the heater body. The screen is thus held in place yet may be easily removed when desired.

As illustrated, it is seen that the fan motor and fan assembly, are directly mounted with brackets to the heater body. Thus, I have succeeded in mounting all the components of the heater directly to the heater body, without the use of an inner liner. I have thus simplified construction of the heater at the same time making it more economical to manufacture and facilitating access to the heater components.

If desired, a timer (not shown) may be incorporated in the electrical circuit to cut off the flow of current to the ribbon element and the motor at the end of a preselected period of time.

The sides of the heater body are preferably provided with apertures 53 below the fan intake to insure that the supply of air to the fan will not be less than fan delivery.

The procedure for making a moisture test will now be described. The empty sample container 10 is placed on the platform of the special scale 20. The container 10 has a preferred tare weight of approximately 115 gms., specially designed for use on this special scale. The pointer 25 is adjusted to align with the uppermost graduation, identified as moisture percent graduation 100, on the percent moisture scale by adjusting the knob 26. Of course, it is understood that the special scale face 21 may be adjusted relative to the pointer 25, in a modified structure, to provide the same relative adjustment without the use of knob 26. The sample container is then filled with a sample until the scale pointer 25 registers zero on the moisture percent scale. An effort should be made to distribute the sample uniformly over the foraminous bottom of the sample container to assure uniform and thorough drying. The container is lifted off the scale platform and placed on heater unit 30 and the ribbon heating element 38 and the motor 26 are energized to supply upwardly directed hot air. Thirty five minutes are usually allowed for drying the sample before it is removed from the heater and again placed on the special scale. Moisture content of the sample specimen is read directly on the special scale face and may be compared with the ideal moisture content with the particular crop. If the degree to which the moisture content matches the most preferred moisture content for that particular crop, is an indication as to whether or not the crop to be harvested is at an optimum moisture level. The dry matter content is read directly on the dry matter scale identified by numerals 24.

In the event that the test is permitted to continue beyond the preferred 35 minute period, no harm can come to the sample. An accurate percentage reading after an extended period of elapsed time can still be made with the use of a timer even after one or two hours. This is true only because of the fact that all three parts of this moisture tester are all held in a definite relation to each other to along with the thermostat, provide controlled heating.

The three components of the moisture testing apparatus — the sample container 10, the special scale 20 and the heater unit 30 — are designed to be sold as a unitary composite package for the farmer to use as a unit so that he may quickly, inexpensively and accurately determine the moisture content of his crops.

The heater 30 with motor, fan, coil and thermostatic control constitute a heater which is an integral part of this tester unit and must be made in the relationship of component parts proposed with fan, coil, thermostat, and louver type vents fixed in the relation illustrated to ensure the proper moisture removal by the unidirectional forced passage of uniformly distributed dry heated air at a predetermined temperature at a fixed distance through a sample in a given length of time.

The ribbon heating element is interlaced over a major portion of the cross-sectional area of the heater so that is serves to contact essentially all of the air flowing therethrough, and at the same time because of the manner in which the ribbon element is interlaced, the ribbon heating element provides a diffusing effect on the air thus contributing to more efficient heating. The repeated heating and cooling of the ribbon element, and the expected expansion and contraction thereof, do not displace the interlaced disposition of the ribbon element because of the constant tension under which the spring means 46 maintain it.

It is now quite clear that, with the moisture testing apparatus of this invention, a higher temperature air stream may be obtained to dry the sample in the container, the temperature may be controlled more accurately because of the unique manner in which the thermostat sensing element is housed, and the entire assembly may be disassembled for cleaning or for inspection and reassembled without the disadvantage of having to fit an inner liner.

Modifications, changes and improvements to the form of the invention herein disclosed, described and illustrated may occur to those skilled in the art who come to understand the principles and precepts thereof. Accordingly, the scope of the patent issued hereon should not be limited to the particular embodiments of the invention set forth herein, but rather should be limited by the advance by which the invention has promoted the art.

I claim:

1. In a three-component moisture testing apparatus including a sample container, a scale and a heater unit for providing unidirectionally flowed hot air through said sample, wherein said heater unit includes a fan and fan motor, heating element and thermostat, inlet cool air screen means to filter incoming air and outlet hot air screen means to filter and diffuse heated air, removably fixed in a heater body, the improvement comprising a ribbon heating element interlaced between a pair of horizontal, parallel, spaced-apart ceramic supports, said ribbon heating element extending for and aft the center line of said heater body over a major portion of the cross-sectional area of said heater body, a pair of oppositely disposed mounting brackets fixedly attached to said heater body, internally thereof, to support ceramic supports, spring means for biasing one of said ceramic supports to one of said mounting brackets so as to maintain said heating ribbon element interlaced under tension at all times, said thermostat being mounted above said heating element immediately adjacent to said inlet screen means, and said thermostat includes a sensing element shielded by a metal shield and enclosed in a ceramic material and is responsive to changes in temperature in the sample container while being essentially non responsive to the direct radiant heat from said heating element.

2. The moisture testing unit of claim 1 wherein said fan motor, mounting brackets, thermostat, and inlet and outlet screen means are fixedly mounted directly to said heater body.

3. The moisture testing unit of claim 2 wherein said inlet cool air screen means is removable from below said heater body, and said outlet hot air screen means is removable from the top of said heater body.

* * * * *